United States Patent [19]

Pearson

[11] Patent Number: 5,173,257
[45] Date of Patent: Dec. 22, 1992

[54] CONTINUOUS PROCESS AND APPARATUS FOR THE SEPARATION OF RECYCLABLE MATERIAL FROM AND THE DISINFECTION OF INFECTIOUS MEDICAL WASTE

[76] Inventor: Erich H. Pearson, 925 Oakwood Ct., Glen Ellyn, Ill. 60137

[21] Appl. No.: 699,202

[22] Filed: May 13, 1991

Related U.S. Application Data

[63] Continuation-in-part of Ser. No. 679,601, Apr. 3, 1991, Pat. No. 5,116,574.

[51] Int. Cl.$^5$ ............................................. A61L 2/00
[52] U.S. Cl. ........................................ 422/3; 210/173;
210/195.3; 210/252; 210/295; 210/513;
210/760; 241/DIG. 38; 241/152.1; 422/28;
422/32; 422/38; 422/140; 422/224
[58] Field of Search ............... 422/37, 38, 3, 2, 224,
422/26-29, 140; 210/749-760, 764, 173, 195.3,
252, 513, 295; 209/3, 10, 211; 241/152 R, 152
A, 20, 21, 24, 29, 46.17, 69, DIG. 38; 261/DIG.
70, DIG. 42

[56] References Cited

U.S. PATENT DOCUMENTS

| | | | |
|---|---|---|---|
| 3,547,577 | 12/1970 | Lovercheck | 241/DIG. 38 |
| 3,549,528 | 12/1970 | Armstrong . | |
| 3,772,188 | 11/1973 | Edwards | 210/173 X |
| 3,778,229 | 12/1973 | Webster et al. | 422/98 |
| 3,790,091 | 2/1974 | Law et al. | 241/DIG. 38 |
| 3,817,458 | 6/1974 | Gilberto | 241/20 X |
| 3,876,157 | 4/1975 | McIntire et al. | 241/24 X |
| 3,897,330 | 7/1975 | Rhys | 209/3 X |
| 4,160,722 | 7/1979 | Marsh | 241/20 X |
| 4,194,968 | 3/1980 | Pfalzer et al. | 209/3 |
| 4,234,560 | 11/1980 | Kuerten et al. | 422/24 X |
| 4,313,827 | 2/1982 | Ratigan et al. | 210/136 |
| 4,578,185 | 3/1986 | Wilson et al. | 210/85 |

Primary Examiner—Robert J. Warden
Assistant Examiner—Krisanne M. Thornton
Attorney, Agent, or Firm—Roper & Quigg

[57] ABSTRACT

A process and apparatus for continuously treating infectious waste, which comprises: (a) introducing bulk unseparated infectious waste material into a receiving container means, the receiving container means adapted to receive a flow of disinfectant such that the receiving container means remains substantially free of infectious contaminants; (b) shredding the waste material by a primary shredding means; (c) separating the shredded waste material from waste residue in a separation tank means having a predetermined fluid level thereby producing a waste slurry; (d) pumping the waste slurry into a reactor vessel means; (e) contacting the waste slurry with a disinfecting fluid in the reactor vessel means for a sufficient amount of time to disinfect the waste slurry; and (f) dewatering the disinfected waste slurry to recover solid disinfected waste material.

The process and apparatus is also adapted to separate and treat recyclable materials, such as pulpable materials, glass, metal, and the like, found in the incoming waste stream.

27 Claims, 1 Drawing Sheet

CONTINUOUS PROCESS AND APPARATUS FOR THE SEPARATION OF RECYCLABLE MATERIAL FROM AND THE DISINFECTION OF INFECTIOUS MEDICAL WASTE

This application is a continuation-in-part of my application entitled Continuous Treatment Process and Apparatus For The Disinfection Of Infectious Waste, Ser. No. 679,601, filed Apr. 3, 1991 the specification, drawings, and claims of which are incorporated by reference for all purposes as if fully set forth herein now U.S. Pat. No. 5,116,574.

BACKGROUND OF THE INVENTION

1. Field of the Invention

The invention relates to a process and apparatus for the separation and treatment of infectious waste in a rapid, cost efficient manner, with materially less environmental impact than the historically practiced art. More particularly, the invention relates to an apparatus and method for the continuous treatment of biologically contaminated medical waste, such as syringes, gowns, bedding, containers, bandages and other liquid or solid materials which may be contaminated with infectious bacterial and viral agents, or with organic contaminants such as chemopharmaceuticals, oxidizable solvents, and the like, in a reactor utilizing gas oxidation. The process and apparatus can simultaneously be used to recover recyclable materials obtained from the incoming waste stream.

2. Description of the Prior Art

The disposition of infectious waste is an issue which has received considerable attention among governmental environmental agencies and the public and within the waste disposal industry. Inappropriate disposal practices, as evidenced by infectious medical waste washing up on the beaches of oceans and lakes, as well as being found in ordinary trash containers in public areas, supports the concern that currently practiced treatment and disposal methods are inadequate to handle, in a safe, cost effective manner, the volume of infectious waste being generated today. A process to treat economically large volumes of infectious medical waste in an environmentally acceptable fashion not heretofore used to treat such waste, is therefore needed.

Historically, most infectious waste has been treated by incineration, with the incineration residue thereafter being landfilled or dumped in the oceans. However, recent studies performed on emissions generated from the combustion of medical waste, even from facilities equipped with advanced air pollution control equipment, have demonstrated consistent emission of priority metals, acid gases, and carcinogenic organics such as 2, 3, 7, 8 furans and dioxin. (United States Environmental Protection Agency, *Hospital Waste Combustion Study*, December, 1988). It is the potential toxicity of emissions from medical waste incineration which has driven the capital and operating cost of incineration and pollution control equipment beyond the reach of most hospitals needing to replace old, inefficient, uncontrolled units. Controversy relating to incinerator emissions has also resulted in substantial public opposition to the construction of private or commercial incineration facilities. The consequence has been that demand for the treatment of medical waste has exceeded available supply, and commercial incinerators have, in instances, overcharged the generators of medical waste. This creates an even greater potential for illicit disposal.

Another method traditionally used for decontamination involves steam sterilization in autoclaves. However, autoclaves are less appropriate for economically treating large volumes of infectious waste, and their consistent effectiveness on certain microorganisms, given the unpredictable composition and density of medical waste, has not been fully established. Further, autoclaves do not by themselves change the inherent visual appearance of waste, resulting in uncertainty and fear among those persons responsible for its subsequent handling. Many cases have been reported of autoclaved waste being rejected at landfills.

Others have attempted liquid chemical disinfection of medical waste simultaneously with comminution in high speed hammermills. For instance, U.S. Pat. No. 3,926,379 teaches a continuous process for the decontamination of solid items of comparatively small size, such as hypodermic syringes. This material is introduced through a feed tube to a hammermill, along with a disinfectant liquid delivered by pump. Pulverized solid waste then drops to a bag or drawer. Disinfectant drains from the bag and is reused. However, with this device the potential for microbial aerosols exists, as well as the inability to assure that the disinfectant solution has not become neutralized and therefore inactive. Finally, the device is limited to solid, friable objects of small size; it is not suitable for bulk, loose wastes as received from hospitals.

U.S. Pat. No. 4,618,103 discloses a continuous process wherein solid medical waste is treated with disinfectant liquid during comminution in a high speed hammermill. Waste is manually introduced through a rotatable door along with disinfectant solution. After passing through the hammermill, waste drops to a settling/separation tank, from which disinfectant solution is discharged continuously to a sewer, and solid residue is removed manually. As in U.S. Pat. No. 3,926,379, this method appears intended for small, solid objects in limited quantity; it is therefore not suitable for large volumes of medical waste.

U.S. Pat. No. 4,619,409 teaches a continuous process wherein solid medical waste is treated with disinfectant liquid during comminution in a high speed hammermill. Waste material is continuously conveyed to a second conveyor which operates an automatic door ahead of the hammermill. Milled waste drops to a settling/separation tank, from which disinfectant solution is discharged continuously to a sewer, and solid residue is removed manually. The method disclosed by this patent is not readily suitable for tonnage quantities of medical waste, owing to the need for manual removal of milled waste from the settling tank, thereby placing humans in contact with the material.

U.S. Pat. No. 4,578,185 teaches another continuous process wherein solid medical waste is treated with disinfectant liquid simultaneously with comminution in a high speed hammermill.

This system is designed for greater volumes of waste than the previous patents cited which utilize a high speed hammermill. However, as in the previous patents cited above, hammermills are most suitable when applied to friable (breakable) materials, but in practice have not proven efficient or effective in achieving particle size reduction with non-friable materials, such as sheet plastic or woven synthetics, neither of which can easily be fractured at standard conditions. Sheet plastics and woven materials comprise a substantial percentage of contaminated medical waste.

Also, as in the previous patent cited above, there is no ability to assure the effectiveness of decontamination on a continuous basis, and none of these patents provide, by themselves, an efficient method of generating treated, recyclable by-products. Further, as in the other patents cited above utilizing high speed hammermills, treatment and comminution occur simultaneously; no means for controlled contacting with disinfectant over a defined retention period is provided. Finally, as in the previous patents cited, there does not exist the ability to treat other liquid organic wastes typically found among medical waste, for instance chemopharmaceutical materials or solvents, prior to discharge to a municipal sewer.

Applicant's prior U.S. Pat. No. 4,884,756 discloses an apparatus for the treatment of medical waste on a continuous process basis. However, applicant's prior apparatus is not suitable for gas oxidation using a reactor vessel series for the disinfecting of medical wastes, nor is there the ability for improved quality control of the treatment process with applicant's prior apparatus as there is with the continuous treatment process of the instant invention. Finally, the technology disclosed by this prior patent cannot separate the waste stream by component to produce suitably recyclable materials.

Applicant has overcome the above-discussed shortcomings of the prior art by providing a continuous process for separating and disinfecting infectious waste, such as infectious medical waste. The process generally comprises:

(a) introducing bulk unseparated infectious waste material into a receiving container means, said receiving container means adapted for receiving a flow of disinfectant such that said receiving container means remains substantially free of infectious contaminants;

(b) shredding the waste material by a primary shredding means;

(c) separating components of the shredded waste material in a separation tank means having a predetermined fluid level thereby producing at least one waste slurry stream;

(d) transferring the waste slurry stream into a reactor vessel series means;

(e) contacting the waste slurry stream with a disinfecting fluid in the reactor vessel series means for a sufficient amount of time to disinfect the waste slurry stream; and (f) dewatering the disinfected waste slurry stream to recover solid disinfected waste material for recycling.

In addition, the process of the present invention optionally provides additional shredding means located downstream from the separation tank means for further shredding the waste materials in the waste slurry stream, when and if necessary. The disinfectant preferably comprises ozone in gas phase and/or in aqueous solution.

As noted, other shredding means, such as for example secondary and tertiary shredding means, may be employed if necessary to further reduce the size of particles in the waste slurry stream prior to pumping the same into the reactor vessel means. All of the shredder means utilized in the process of the invention are preferably commercially available low speed, high torque rotary shear shredders. The secondary and tertiary shredders, if employed, are preferably adapted for in-line submerged applications, because these shredders are disposed below the fluid level of the separation tank means.

The waste slurry stream (which may comprise from about 1% to about 10% by weight shredded solids) is pumped for a sufficient amount of time to allow the waste slurry stream to fill the reactor vessel means to a predetermined level.

Ozone gas, in a concentration of from about 0.5% to about 10% by weight, is preferably employed as the disinfecting fluid in the reactor vessel means. In order to maximize contact with the ozone gas, the waste slurry stream may be flowed through a gas contactor, associated with the reactor vessel, in a direction opposite to the buoyancy of ozone gas bubbles in the contactors, although co-current or cross-current flows are equally useful if the residence time and turbulence of the waste slurry in the contactor means is adjusted accordingly. For example, when using counter-current flow, the waste slurry is flowed through the contactor at a rate which preferably exceeds the terminal velocity of the ozone gas bubbles. Ozone gas bubbles having an average diameter of about 1 millimeter or less are preferably utilized.

The disinfection process is preferably monitored continuously by an offgas analyzing means associated with the reactor vessel means, to assure that sufficient disinfecting fluid is introduced into and maintained in the reactor vessel means. Contacting times from about 5 to about 45 minutes have been found to be sufficient to effectively disinfect typical infectious waste materials.

The present invention also contemplates an apparatus for the treatment of infectious waste. The apparatus comprises:

(a) a receiving container means for receiving bulk infectious waste material, said receiving container means being adapted to receive a flow of disinfectant from a disinfectant means for disinfecting the surfaces of said receiving container means;

(b) a primary shredding means in association with the receiving container means, for reducing the particle size of the infectious waste material;

(c) a separation tank means connected to the primary shredding means, for separating components of the shredded waste material and forming a waste slurry stream, the separation tank means having a fluid filling means for filling the tank means to a predetermined level;

(d) a reactor vessel means for disinfecting the waste slurry stream, the reactor vessel means preferably comprising:

(i) at least two reactor vessels, the first of which is disposed in a position to receive the waste slurry stream from the separation tank means and the remainder of which is disposed to communicate in series relationship, with such series commencing with the first reactor vessel, each such reactor vessel having associated therewith a gas contactor;

(ii) a disinfecting fluid generating means connected with each of the contactors, for continuously introducing a disinfecting fluid into the contactor and the reactor vessel means;

(iii) a recirculation port means associated with at least two reactor vessels, for allowing the waste slurry stream to flow through each of the at least two reactor vessels at a rate greater than the slurry generation rate; and (iv) an analyzing means associated with the reactor vessel means, for continuously monitoring the amount of disinfecting fluid introduced by the disinfecting fluid generating means and the amount of disinfecting fluid utilized in the reactor vessel means; and (e) dewatering means associated with the reactor vessel means, for recovering solid, disinfected waste material from the disinfected waste slurry.

The apparatus may include secondary and tertiary shredding means, as described above, if needed to provide a waste slurry stream having a further reduced particle size.

The reactor vessel means which forms an essential part of the subject apparatus generally comprises from about 1 to about 10 reactor vessel units connected in series. The number of vessels employed will depend on a number of factors described in detail below. Each reactor vessel includes a gas contactor, which may extend longitudinally from the top of the reactor vessel toward the bottom thereof, where the contactor is in connecting relation with the transfer pump means.

The disinfecting fluid generating means used to disinfect infectious waste according to the present invention preferably comprises an ozone generator. The ozone gas disinfecting fluid may be generated from either compressed air or high purity oxygen.

BRIEF DESCRIPTION OF THE DRAWING

For a more complete understanding of this invention, reference should be made to the drawing, as briefly described below.

DESCRIPTION OF THE PREFERRED EMBODIMENTS

Figure 1:
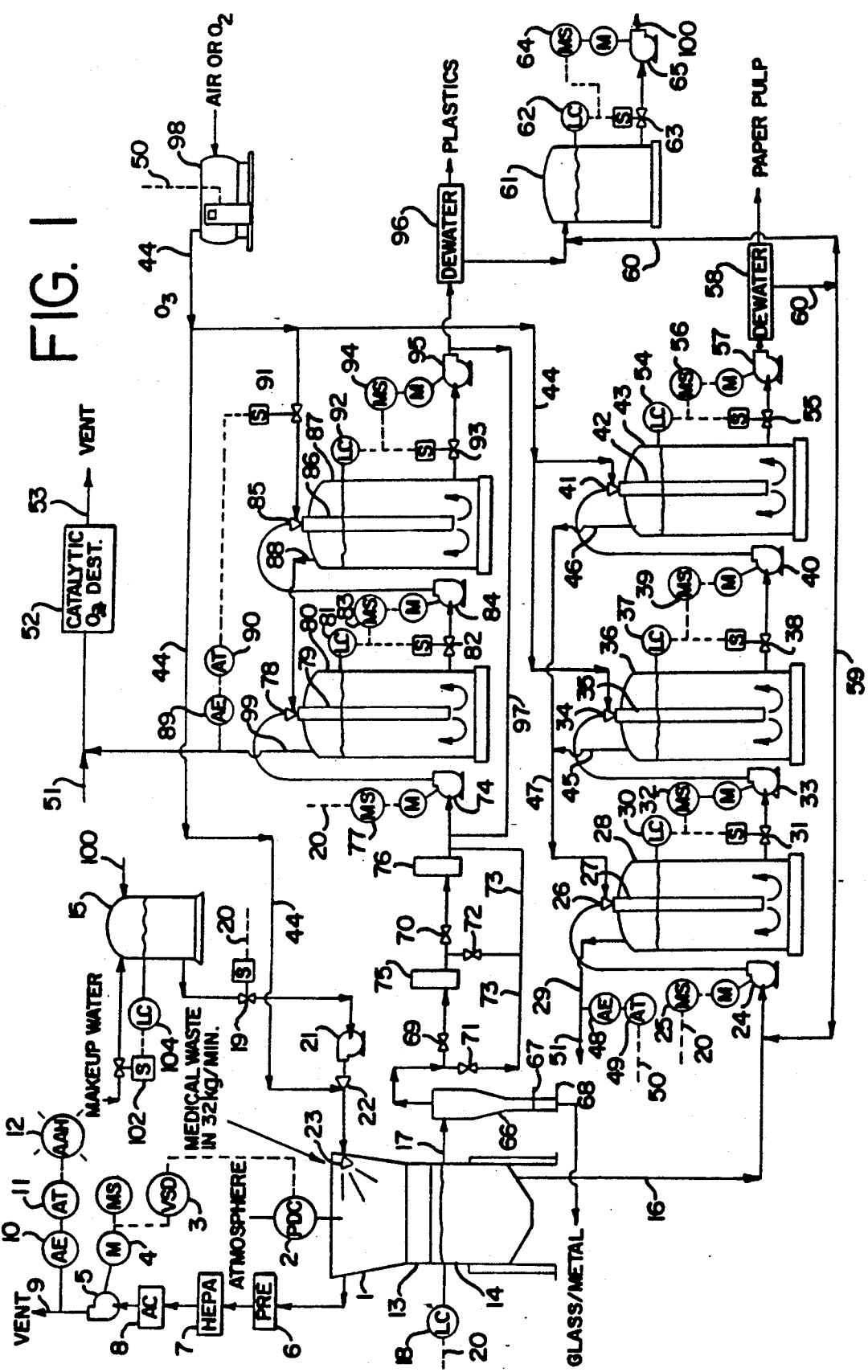
FIG. 1 is a schematic representation of the particle size reduction and reactor vessel apparatus and continuous process utilizing gas oxidation for the separation and the treatment of infectious waste materials according to the present invention.

Referring in detail to FIG. 1, there is illustrated a particle size reduction apparatus and process used to reduce the particle size of infectious waste material, which waste material will subsequently be separated into recyclable components and disinfected using the reactor vessel apparatus and ozone gas oxidation process also shown in detail in FIG. 1.

Referring to FIG. 1, bulk infectious medical waste (not shown) is introduced to receiving hopper 1. Air pressure within hopper I is maintained negative relative to ambient air pressure by pressure differential controller 2. This controller 2 transmits proportional voltage or current to variable speed drive 3, which modulates the speed of motor 4 driving ventilation fan 5. Alternatively, a manual or automatically actuated mechanical damper (not shown) may be used to regulate the volume of air drawn by ventilation fan 5. The speed of ventilation fan 5 is sufficient to maintain a flow of air into hopper 1 at a velocity adequate to minimize the escape of microbial aerosols and odors from the hopper infeed opening. Of course, the exact air velocity is dependent on the nature of the waste materials, the size of the infeed opening to the hopper 1, and other factors as will be appreciated by one skilled in the art.

Air induced from hopper 1 by ventilation fan 5 is drawn through prefilter 6, HEPA (High Efficiency Particulate Arresting) filter 7, and activated carbon filter 8, prior to release to the atmosphere through duct 9. These filters assure that the exhausted air is substantially free of contaminated aerosols, odors, and trace ozone.

Ozone not adsorbed onto carbon filter 8 is detected by analysis element 10, which transmits an electrical signal to analysis transmitter 11, energizing alarm 12. Alarm 12 preferably signals any condition in which ozone, as detected by analysis element 10, exceeds one-half the Short Term Exposure Limit for ozone (STEL), or 0.15 ppm, as established by ACGIH (1989). However, alarm 12 may be adjusted to signal an alarm condition at any ozone concentration within the detection range of analysis element 10.

Bulk infectious waste within hopper 1 may be fed by gravity, or other conveyor methods (not shown), from hopper 1 to primary shredder 13. Primary shredder 13 is preferably a low speed, high torque rotary shear shredder, Which is suitable for coarsely shredding high concentrations of nonfriable materials commonly found in medical waste, such as sheet plastic and woven or synthetic materials. Primary shredder 13 is designed with sufficient torque to shred metallic objects which also could be found in medical waste. Primary shredder 13 may be any of several suitable commercially available rotary shear shredders, such as model number 1575E from SSI Shredding Systems, Inc., Wilsonville, Oreg.

Coarsely shredded waste material from primary shredder 13, which may have particle sizes of about 4 cm or smaller, discharges vertically downward to pulper 14. In pulper 14, the shredded waste materials are saturated with water, which may be supplied through a line (not shown) from makeup tank 15, to form a slurry containing from about 1% to about 16%, and preferably about 5%, suspended solids by weight. Pulper 14 is a commercially available apparatus for repulping and separating the paper fiber component of incoming waste material. Suitable pulpers are commercially available from several sources, including the Black Clawson Company, Middletown, Ohio. Paper pulp is automatically withdrawn from pulper 14, through a screen located at the bottom of pulper 14, through duct 16, and treated as described hereinafter. Nonfibrous and unpulpable materials are withdrawn from pulper 14 through duct 17, and treated as described hereinafter.

The repulping of paper and extraction of nonfibrous contaminants is practiced by many paper mills. However, in the case of medical waste the concentration of nonpaper contaminants may comprise 50% by weight of the incoming waste; this greatly exceeds the 5%-10% maximum contaminants normally encountered in paper milling operations. Therefore, the prime consideration in the sizing of conventional pulpers for the application described in the present invention is not pulping capacity, but rather the capacity for the extraction of an excessive concentration of nonfibrous and unpulpable contaminants.

Slurry level within pulper 14 is maintained at a predetermined level by level controller 18. Level controller 18 transmits proportional current or voltage to proportioning valve 19 via electrical line 20, which modulates the flow of makeup water through pump 21. Alternatively, level controller 18 may transmit a proportioning signal to a variable speed drive motor (not shown) driving makeup pump 21.

Makeup pump 21 draws water from makeup tank 15 and forces this water through eductor 22. Eductors are commercially available devices which are suitable for providing efficient mass transfer between two compressible fluids. Eductors are venturi-type devices which include an inlet convergent section, typically conical, a venturi orifice of a diameter generally about 25%–40% of the diameter of the inlet, and a gradually divergent section after the venturi orifice. The accelerated velocity of a fluid passing through the venturi orifice decreases the pressure of the fluid according to Bernoulli's law; this low pressure may then be employed to induce and mix secondary fluids. Release from the venturi orifice to the divergent section of the eductor results in high turbulence and, thus, efficient mixing of the two fluids. In the process of the present invention, eductors have been found to achieve mass transfer rates of ozone gas into water of up to about 99%. Eductor 22 may be any of several commercially available eductors, ejectors, jet pumps, or injectors, such as those from Mazzei Injector Corporation, Bakersfield, Calif. However, other commercially available means for achieving ozone mass transfer may also be employed, including bubble columns and in-line static mixers, as one skilled in the art will appreciate.

Ozone gas, generated by ozonator 98 and distributed in manifold 44, is induced into and mixed with water within eductor 22. This ozonated water is then sprayed through nozzle 23 into receiving hopper 1 at a rate, regulated by level controller 18, sufficient to maintain a predetermined slurry level within pulper 14. Nozzle 23 is designed and located to continuously expose the interior surfaces of hopper I to ozonated makeup water from makeup pump 21. Ozonated water has a high disinfecting efficacy, and thus maintains a substantially aseptic environment within hopper 1. Any ozone still in gas phase (e.g., undissolved in water from eductor 22) functions substantially to neutralize odor and microbial aerosols within hopper 1.

Alternatively, the ozonated water from makeup pump 21 can be fed continuously or intermittently to nozzle 23, with the outflow from eductor 22 also being directed via a line (not shown) to pulper 14 to maintain a predetermined fluid level within pulper 14 wherein the waste slurry is formed.

Once the waste slurry reaches a predetermined level in pulper 14, separated paper pulp in slurry form is induced from pulper 14 by transfer pump 24, which is started by an electrical signal via electrical line 20 from level controller 18 to motor starter 25.

Referring again in detail to FIG. 1, there is illustrated the preferred embodiment of the inventive continuous treatment apparatus and process utilizing gas oxidation in a reactor vessel apparatus and process.

As shown in detail in FIG. 1, separated paper pulp in slurry form from the shredding apparatus and pulping process is pumped, via transfer pump 24 through at least one reactor vessel, and preferably a series of reactor vessels, each designed to achieve a percent reduction of resident microorganisms. The actual number of treatment stages is determined by: (1) the quantity of microorganisms in the untreated waste, as measured by population or concentration in standardized units, such as Colony Forming Unit per milliliter (CFU/ml); (2) the quality of microorganisms in the untreated waste, as measured by the known resistance to neutralization by chemical oxidation for the specific species in question; (3) the degree of disinfection desired; (4) the presence of chemical interferences in the waste slurry, such as organic constituents which consume ozone at variable rates, which could individually or in the aggregate reduce the quantity of ozone available to neutralize microorganisms in any given treatment stage; and (5) the presence of mechanical interferences, such as incomplete mixing, or the availability of fine adsorbent particles providing large adsorbing surface areas, which tend to shield microorganisms from exposure to disinfectants.

Treated slurry may technically be safe for subsequent handling without achieving a 100% reduction during the treatment process; however, one skilled in the art will appreciate that additional treatment stages may be employed to achieve sterility, if that is the desired objective.

According to one preferred aspect of the invention (shown in FIG. 1), three reactor vessels are connected in series to form the disinfecting stage of the invention applied to paper pulp and other fibrous materials in slurry form. As previously described, from 1 to about 10 reactor vessels may be employed as the reactor vessel means for the disinfecting stage of the invention applied to paper pulp and other fibrous materials. These reactor vessels are sealed from the external environment, but permit the flow of slurry between individual vessels, as described below. Modeling studies indicate that six passes through a gas contactor, and a total retention time of about 5 to about 45 minutes, preferably on the order of about 30 minutes, is sufficient to achieve decontamination of fibrous solids in slurry suspension under most conditions.

In order to initiate the disinfecting stage of the inventive process, transfer pump 24 directs the paper pulp waste slurry through mixer 26. Mixer 26 (as well as mixers 34 and 41) may be an eductor or an in-line static mixer, or a combination of such, both types commercially available from a number of sources and well known in the art. In potential large scale commercial applications, the slurry may be flowed through mixer 26 at a rate of about 1460 kg/min. and a pressure of 4.2 kg/cm$^2$, in order to maintain slurry velocity of about 49 meters/second across the eductor venturi orifice of mixer 26. These specifications are applicable for an eductor type mixer having an orifice diameter of 2.5 cm, which is about the smallest orifice diameter which would reliably pass typical slurried waste containing solid particles up to a diameter of about 12 mm. Larger eductors may readily be used at correspondingly higher flow rates, and smaller eductors may be used at correspondingly lower flow rates, with the principal point being that the size of the eductor orifice must pass the largest particles in the, slurry so that clogging is avoided. Particle size in the paper pulp slurry is largely, but not entirely, determined by the sizing of the screen located at the bottom of pulper 14, through which pulped paper is induced by transfer pump 24. The principles of operation for mixer 26 are identical to those for eductor 22, described above. Eductors are suitable for use as mixing devices in the present invention because they do not employ static or dynamic elements which could collect solids and eventually obstruct flow, while still providing efficient mixing and mass transfer in a turbulent flow regime. However, as noted above, other types of in-line high shear mixers, emulsifiers, and homogenizers may also be employed, depending on the actual composition of the waste slurry.

Mixer 26 discharges vertically downward through reactor tube 27, located along the axis of reactor vessel 28. Reactor tube 27 may also be located exterior to vessel 28, provided that its discharge into vessel 28 does not create undesirable vortices and overly laminar flow.

Slurry velocity within reactor tube 27 is about 1.1 meters/second, or any velocity sufficiently greater than the terminal velocity for ozone gas bubbles (about 0.3 to about 0.5 meters/second for 1 mm bubbles).

The efficient mixing of mixer 26, the presence of ozone gas bubbles averaging about 1 mm diameter (to maximize surface area per unit mass of ozone gas), the flow of slurry within reactor tube 27 counter to the buoyancy of ozone gas bubbles, ad the approximate 4 second slurry retention time within the reactor tube all combine to provide intimate liquid/gas mixing liquid and gas/solids contacting, mass transfer, and efficient decontamination in a turbulent flow regime.

Slurry is discharged at the bottom of reactor tube 26 in a region above the base of reactor vessel 28. Ozone gas bubbles coalesce as they rise to the surface of the slurry within vessel 28 and are evacuated through port 29.

When the slurry reaches a predetermined level in reactor vessel 28, level controller 30 transmits an electrical signal to the actuator for valve 31, and to motor starter 32, to start transfer pump 33. Pump 33 directs slurry through mixer 34 and reactor tube 35, serving reactor vessel 36, in the same manner as delineated above for reactor vessel 28. When the slurry reaches a predetermined level in vessel 36, level controller 37 transmits an electrical signal to the actuator for valve 38, and to motor starter 39, which starts transfer pump 40. Pump 40 directs slurry through mixer 41 and reactor tube 42, located along the axis of reactor vessel 43 in the same manner as described for reactor vessel 28.

Ozone gas is generated from ozonator 98 at a rate of about 70 grams $O_3$ per minute and at a concentration of about 0.5% to about 10% by weight, preferably about 2% by weight (if generated from compressed air), or about 5% by weight (if generated from high purity oxygen).

It will be understood that using lower concentrations of ozone will increase the contact time required to destroy bacterial and viral microorganisms, and using higher concentration of ozone will reduce the necessary contact time.

Ozone is delivered from ozonator 98 into ozone distribution manifold 44. Manifold 44 delivers ozone gas simultaneously to mixers 34 and 41, serving reactor vessels 36 and 43 respectively. Offgas from vessels 36 and 43 is vented through ports 45 and 46 respectively into manifold 47. At this point approximately 5% by weight of the ozone gas originally introduced to mixers 34 and 41 remains. The rest, or about 95%, has been lost to disinfection and other oxidation reactions, and to natural decomposition to oxygen. Offgas in manifold 47 is delivered to mixer 26 serving reactor vessel 28. In this vessel, waste slurry will be preconditioned (i.e., partially disinfected) by utilizing almost all the remaining ozone gas. Offgas from reactor vessel 28 is vented through port 29.

Analysis element 48 continuously measures the ozone concentration in the offgas from reactor vessel 28, and analysis transmitter 49 regulates the rate of ozone production from ozonator 98 by transmitting proportional voltage or current through line 50 to ozonator 98 so that a slight excess of ozone, about 1.0 ppm, is maintained in the offgas from reactor vessel 28. An excess of ozone at this point assures that sufficient ozone is available for decontamination throughout the system, and that ozone is employed with maximum efficiency.

If desired, ozone may also be introduced to reactor vessels 28, 36, and 43 entirely in parallel rather than in series, e.g., from a common manifold serving mixers 26, 34, and 41, respectively. Offgas would then also be directed to common or discrete offgas treatment. However, the introduction of ozone in parallel may not result in as high an ozone utilization efficiency.

After being analyzed for ozone concentration, offgas from reactor vessel 28 is directed via duct 51 through ozone destruct unit 52, which may consist of any of several commercially available $O_3$ decomposition systems employing heat and/or catalysts to decompose ozone to oxygen at an efficiency of at least about 99%. After treatment, gases may be exhausted through vent 53. Gas analysis devices similar to analysis element 10, analysis transmitter 11, and analysis alarm 12, may be installed in line to vent 53 to assure that ozone is reduced to environmentally acceptable levels.

Reactor vessel 43 continues to fill to the elevation of level controller 54. At this point, level controller 54 transmits an electrical signal to the actuator for valve 55, and to motor starter 56, to start discharge pump 57. Pump 57 transfers slurry from reactor vessel 43, at a flow rate equivalent to the flow rates for transfer pumps 24, 33 and 40; to dewatering system 58.

Flow rates for transfer pumps 24, 33, and 40 are determined by the flow specification for mixers 26, 34, and 41 respectively. If the flow rate for these mixers exceeds the rate at which slurry is being generated from pulper 14, water recycle line 59 may be employed to receive water effluent from the dewatering system 58 via line 60 and associated valving (not shown) to furnish the water deficit. Slurry may be recycled from any point in the reactor vessel series prior to dewatering system 58, or water may be recycled by using a portion of the effluent from dewatering system 58, as shown. However, the recycling of slurry, from which solids have not been removed, may increase ozone consumption because ozone will continue to react with any oxidizable materials in the slurry. In addition, the unnecessary recycling of paper fibers will reduce fiber quality, as fibers will be broken down due to chemical and mechanical attrition. Therefore, the recycling of water effluent only, if recycle is necessary, may be advantageous.

For example, the introduction of about 32 kg/min. of bulk medical waste into hopper 1 will yield about 640 kg/min. of slurry formed in pulper 14, if the solids concentration in slurry suspension is maintained at 5% by weight. Of this, about half, or 320 kg/min., will be extracted through line 16 by transfer pump 24 to be treated in the reactor vessel series. If transfer pump 24 is required to deliver 1460 kg/min. through mixer 26, a recycle will be required via line 59 of the difference between the quantity of slurry flowing through line 16 and that required by mixer 26, or in this example about 1140 kg/min. As noted above, eductors with less cross sectional area at the orifice, or other types of mixers, may require less or no recycle.

Dewatering system 58 may be any of several commercially available liquid/solid separation devices, including, but not limited to, centrifuges, belt filters, vacuum filters, filter presses, gravity filters, extruders, flash driers, radiant driers, etc., depending on the final retained moisture content desired.

Liquid filtrate from dewatering system 58 is transferred by gravity or pump (not shown) via line 60 to sump tank 61. When water has reached a predetermined level in sump tank 61, level controller 62 energizes the actuator for valve 63 and motor starter 64, which starts sump pump 65. Sump pump 65 directs water from sump tank 61 via line 100 to makeup tank 15. Fresh water is then added to makeup tank 15 through valve 102, the actuator for which is signalled by level controller 104, as needed to maintain a predetermined makeup water level within makeup tank 15. Conventional controls are used to avoid overfilling tank 15.

After dewatering, decontaminated paper pulp is recovered from dewatering system 58. The decontaminated paper pulp is then suitable for recycling into usable products, extrusion (pelletizing) for RDF (Refuse Derived Fuel) or, if necessary, for nonhazardous waste landfill.

As stated above, pulper 14 also extracts nonfibrous, unpulpable materials through duct 17. These materials are separated and treated as described below.

Unpulpable materials extracted from pulper 14 through duct 17 first pass through separator 66. Separator 66 may be any of several types of separators employing gravitational settling or centrifugal force, or a combination of these, to separate heavier solid particles which could inhibit the operation of or damage subsequent shredding stages. FIG. 1 depicts a centrifugal separator, as this type of separator is typically employed in conjunction with pulpers in paper mill operations and can be supplied by pulper manufacturers. Irrespective of the exact nature of the separator 66, it is important that separator 66 be operated to separate only heavier solid objects, such as glass and metal fragments; all other materials should be discharged from separator 66 to assure optimized process efficiency.

Solid objects settle to the base of separator 66, and may be removed as needed by opening and closing valve 67, then opening and closing valve 68. These valves may be operated manually, or automatically with electric or pneumatic actuators (not shown). Glass and metal thus separated from the slurry stream may further be processed employing conventional methods to recover discrete glass and metal constituents for recycling. Much of the metal found in medical waste is alloyed, and consequently has recycling value.

Referring again in detail to FIG. 1, nonfibrous and unpulpable materials discharged from separator 66 may further be cleaned of paper fiber in conventional auxiliary equipment (not shown), utilized in paper mills and available, for instance, from Black Clawson Company, Middletown, Ohio, under the trade name "Select-Purge". This additional step may be desirable to maximize the recovery of paper fiber, and to produce a process stream consisting predominately of plastics. If this auxiliary equipment is utilized, the separated paper fiber from it would be discharged in slurry suspension to duct 16, to be treated, as described hereinabove, with paper pulp extracted directly from pulper 14.

Upulpable waste materials, consisting at this stage chiefly of mixed plastics, may require further particle size reduction to increase surface area so that disinfecting efficiency is maximized. If no additional particle size reduction is required subsequent to the primary stage, as determined by the quality of waste to be treated, secondary and tertiary shredding stages 75 and 76 may be bypassed by closing valves 69 and 72, opening valve 71 and directing the flow of the waste slurry to pump 74 via line 73. If secondary shredding in shredder 75 is required, to produce a smaller particle size, such as for example to about 20 mm, valves 71 and 70 are closed, and valves 69 and 72 opened; the slurry exiting secondary shredder 75 is then directed to pump 74 via line 73. If tertiary shredding in shredder 76 is also required, to further reduce the shredded particle size, such as for example to about 5 mm, valves 71 and 72 are closed and valves 69 and 70 are opened.

Secondary shredder 75 and tertiary shredder 76 are, like primary shredder 13, low speed, high torque rotary shear shredders, which have proven to be the most effective means of achieving size reduction of nonfriable materials. However, secondary shredder 75 and tertiary shredder 76 are designed for in-line, submerged applications. Tertiary shredder 76 may be identical to secondary shredder 75 except for the width of the rotary cutter knives, as cutter width largely determines final shredded product size. Such shredders are commonly employed in municipal wastewater treatment headworks, and are available, for instance, from Disposable Waste Systems, Inc., Santa Ana, Calif.

Although not depicted in FIG. 1, secondary and tertiary shredders 75 and 76 may be arranged in parallel trains, i.e., there may be two secondary and two tertiary shredders. The use of parallel trains may have operational advantages. In this regard, the present invention is not deemed limited to the single train configuration shown in FIG. 1.

Unpulpable solid waste material, now finely divided and in water slurry suspension, is induced through the separation and shredding stages by transfer pump 74. Pump 74 is started by motor starter 77 when water reaches a predetermined level in pulper 14, signalled by level controller 18 via electrical line 20. Transfer pump 74 directs slurry through mixer 78 and reactor tube 79 serving reactor vessel 80 in the same manner as delineated above for reactor vessel 28. When the slurry reaches a predetermined level in reactor vessel 80, level controller 81 transmits an electrical signal to the actuator for valve 82, and to motor starter 83, to start transfer pump 84. Pump 84 directs slurry through mixer 85 and reactor tube 86, located along the axis of reactor vessel 87, in the same manner as delineated above for reactor vessel 28.

Ozone gas, generated from compressed air or high purity oxygen in ozonator 98, is delivered into distribution manifold 44 to mixer 85. The specifications for mixer 85, with respect to flow rate, velocity, pressure, and mixer type, are similar to those for mixer 26 described hereinabove. The offgas from reactor vessel 87, which is depleted of about 90-95% of the ozone present at the inlet to mixer 85, is vented through port 88 and directed to mixer 78. Mixer 78, reactor tube 79, and reactor vessel 80 serve to utilize almost all remaining ozone, and to precondition (i.e., partially disinfect) waste slurry.

Alternatively, ozone gas from ozonator 98 may be directed to mixers 78 and 85, serving reactor vessels 80 and 87 respectively, in parallel rather than in series as shown. However, a parallel introduction of ozone may not yield as high an ozone utilization efficiency as a serial introduction.

Offgas from reactor vessel 80 is vented through port 99, and from there to ozone destruct module 52, as described above for reactor vessel 28. Alternatively, a separate ozone destruct module may be used for offgas from reactor vessel 80 if desired. Analysis element 89, located in the duct between discharge port 99 and ozone destruct module 52, continuously monitors the concentration of ozone in the offgas from reactor vessel 80. Analysis element 89 signals analysis transmitter 90, which transmits proportional voltage or current to proportioning valve 91, located in ozone distribution header 44 at the inlet of mixer 85. The quantity of ozone introduced to the reactor vessel series is thus controlled such that an ozone residual of about 1.0 ppm is maintained in the offgas from reactor vessel 80. This is beneficial to assure that an excess of ozone is available within the reactor vessel series at all times, e.g. that ozone demand will not exceed ozone supply. An ozone inlet concentration to offgas destruct unit 52 of 1.0 ppm will also assure that its exhaust does not exceed OSHA standards for ambient ozone (0.01 ppm), as catalytic ozone destruct units typically achieve 99% decomposition efficiency.

When the slurry has reached a predetermined level within reactor vessel 87, level controller 92 signals the actuator for valve 93, and motor starter 94, which starts discharge pump 95. Pump 95, operating at a rate equivalent to transfer pumps 74 and 84, discharges treated waste slurry to dewatering system 96.

Flow rates for transfer pumps 74 and 84 are determined by the specifications for mixers 78 and 85, respectively. If these flow rates exceed the rate at which slurry is generated from the pulping and shredding apparatus, recycle duct 97 may be utilized to furnish this water deficit. Recycle may be taken from any point in the reactor vessel series, or after dewatering system 96; however, unlike for the paper pulp treatment section of this process, the recycling of slurry containing ground plastic may not be detrimental because plastic is not as readily reactive with ozone as is paper fiber, and therefore may not increase ozone consumption. The recycling of the slurry prior to dewatering will also minimize the size of dewatering system 96.

Dewatering system 96 may be any of several commercially available liquid/solid separation devices, including, but not limited to centrifuges, belt filters, vacuum filters, filter presses, gravity filters, extruders, flash driers, radiant driers, etc., depending on the final retained moisture content desired. Dewatered solids recovered from dewatering system 96 will consist principally of finely ground, mixed plastics. This material may be utilized in the manufacturing of products which can incorporate a percentage of mixed recycled plastic. Alternatively, the material can be disposed in a nonhazardous waste landfill.

FIG. 1 depicts a series of two reactor vessels for the treatment of ground plastics in slurry suspension, and a series of three reactor vessels for the treatment of paper fibers in slurry suspension. The actual number of reactor vessels in series is based on several factors as described hereinabove. However, given equivalent suspended solids concentration, flow rates, contact times per reactor, mixer specifications, ozone concentration and flow, nature of microorganisms, etc., slurried ground plastic should be disinfected more readily than slurried paper fiber, as plastic provides less surface area per unit mass onto which microorganisms may be adsorbed and thus protected. Further, as discussed above, plastic is by itself inherently less reactive with ozone than paper pulp, and as a result plastics introduce less interference with the biocidal activity of ozone.

Of course, anyone practiced in the art can appreciate that the process described above may be employed solely for the disinfection of medical waste if the production of recyclable materials is not desired. In t his case pulper 14 may simply be omitted, and a tank, in which the water level is maintained to form a waste slurry, substituted therefor. However, separator 66, or its functional equivalent, would still be required to remove larger glass and metal objects if subsequent shredding stages are to be employed. The waste slurry, consisting of mixed plastics combined with paper pulp, would be treated in a series of reactor vessels as described above for slurried paper pulp alone.

The following examples are given to illustrate the invention, but are not deemed to be limiting thereof. All percentages given throughout the specification are based on weight, 100% weight basis, unless otherwise indicated.

EXAMPLES 1-14

The following examples are based on modeling studies designed to simulate the reactor vessel series of the invention. The quantity of infectious waste slurry treated and the percent of suspended solids by weight (TSS) is indicated in the table corresponding to each example.

Solids treated consisted of approximately 49% paper and paper products, 49% molded plastics and woven synthetics, and 1% each of glass and metal, the percentages being by weight. This composition is similar to that for infectious medical waste. Inoculum consisted of 250 ml nutrient broth containing the following bacteria species: *Bacillus subtilis, Staphylococcus aureus, Pseudomonas aeruoinosa*, and *Eschericha coli*. The diluted initial concentration of inoculum is indicated as the plate count for the first run of each example (at 0 minutes elapsed time).

Slurry was pumped from the reactor vessel through an ozone contactor, and returned to the vessel. Slurry samples were drawn from a ¾" gate valve located on the pressure side of the pump, with samples placed into 125 ml sterile specimen containers for incubation and plate count analysis by an independent, certified microbiological testing laboratory. Process flow was measured by an ultrasonic, non-intrusive flowmeter. With process flow and elapsed time as measured variables, the number of passes through the ozone contactor at each sampling interval was calculated, as indicated in the tables below.

Ozone was introduced using compressed ambient air as a parent gas for Examples 1-6, and for Example 14. Ozone was introduced using high purity oxygen as a parent gas for Examples 7-13. Ozone concentration by weight ranged from 0.8% to 1.8% for tests using compressed air as a feed gas, and from 2% to 4% using oxygen as a feed gas. Results indicated that the quantity of ozone required to achieve the desired bacterial reduction was somewhat higher when oxygen was used as a feed gas, with ozone generated at higher concentrations.

For Examples 6-11, slurry was deliberately contaminated with known concentrations of organic materials to measure the effect of organic interferences. Although significant, bacterial reduction was not achieved to the desired level for Examples 10 and 11. However, for these tests the slurry was deliberately contaminated with organics (solvents) to a concentration of 1500 ppm by weight, resulting in a COD (chemical oxygen demane) of 8000 mg/l for Example 10 and 7000 mg/l for Example 11. Bacterial reduction was also significant for Example 14, although incomplete. However, during this test frequent plugging of the pump and sample port was experienced, and cross contamination was suspected.

The results of the examples are set forth in Tables 1-14 below. As indicated therein, six passes through an ozone contactor and a net retention time of thirty minutes, in most cases provided effective neutralization of microorganisms in the treated waste materials.

TABLE 1

Example 1
Tank Slurry, kg: 118
TSS, %: 1.5
Parent Gas: COMPRESSED AIR
Organics Added, ppm: NONE

| Sample | Ozone Consumed (grams) | Ozone Conc. (% wt.) | Net Retention (min.) | Plate Count (CFU/ml) | Percent Bacteria Reduction | Passes Through Contactor |
|---|---|---|---|---|---|---|
| Run 1 | 0.00 | 1.476 | 0.0 | 130000 | 0.0000 | 0.00 |
| Run 2 | 0.82 | 1.495 | 0.5 | 350000 | −169.2308 | 0.48 |
| Run 3 | 1.35 | 0.961 | 1.0 | 3000000 | −2207.6923 | 0.93 |
| Run 4 | 1.63 | 0.961 | 1.5 | 700000 | −438.4615 | 1.34 |
| Run 5 | 2.97 | 0.856 | 3.5 | 0 | 100.0000 | 2.94 |
| Run 6 | 4.13 | 0.587 | 5.5 | 0 | 100.0000 | 4.48 |
| Run 7 | 6.67 | 1.437 | 8.5 | 0 | 100.0000 | 6.28 |
| Run 8 | 10.48 | 1.516 | 12.5 | 0 | 100.0000 | 8.65 |
| Run 9 | 14.41 | 1.392 | 16.5 | 0 | 100.0000 | 10.63 |

TABLE 2

Example 2
Tank Slurry, kg: 118
TSS, %: 1.5
Parent Gas: COMPRESSED AIR
Organics Added, ppmw: NONE

| Sample | Ozone Consumed (grams) | Ozone Conc. (% wt.) | Net Retention (min.) | Plate Count (CFU/ml) | Percent Bacteria Reduction | Passes Through Contactor |
|---|---|---|---|---|---|---|
| Run 1 | 0.00 | 1.67 | 0.00 | 2000000 | 0.0000 | 0.00 |
| Run 2 | 2.55 | 1.24 | 2.00 | 1500000 | 25.0000 | 1.40 |
| Run 3 | 5.26 | 1.71 | 4.00 | 50000 | 97.5000 | 2.56 |
| Run 4 | 7.61 | 1.57 | 6.00 | 6000 | 99.7000 | 3.71 |
| Run 5 | 12.51 | 1.64 | 10.00 | 300 | 99.9850 | 6.86 |
| Run 6 | 14.54 | 1.63 | 11.50 | 200 | 99.9900 | 8.01 |
| Run 7 | 15.21 | 1.62 | 12.00 | 6500 | 99.6750 | 8.39 |
| Run 8 | 18.31 | 1.66 | 14.50 | 200 | 99.9900 | 10.36 |
| Run 9 | 21.63 | 1.60 | 17.00 | 300 | 99.9850 | 12.45 |
| Run 10 | 29.17 | 1.65 | 22.00 | 0 | 100.0000 | 17.30 |

TABLE 3

Example 3
Tank Slurry, kg: 113
TSS, %: 2.5
Parent Gas: COMPRESSED AIR
Organics Added, ppmw: NONE

| Sample | Ozone Consumed (grams) | Ozone Conc. (% wt.) | Net Retention (min.) | Plate Count (CFU/ml) | Percent Bacteria Reduction | Passes Through Contactor |
|---|---|---|---|---|---|---|
| Run 1 | 0.00 | 1.76 | 0.00 | 1500000 | 0.0000 | 0.00 |
| Run 2 | 1.17 | 1.13 | 2.00 | 3000000 | −100.0000 | 1.30 |
| Run 3 | 2.51 | 1.10 | 4.00 | 500 | −99.9667 | 2.60 |
| Run 4 | 4.12 | 1.16 | 6.00 | 150 | −99.9900 | 3.89 |
| Run 5 | 5.67 | 1.11 | 8.00 | 0 | 100.0000 | 5.19 |
| Run 6 | 6.89 | 1.17 | 9.50 | 0 | 100.0000 | 6.17 |
| Run 7 | 9.09 | 1.13 | 12.00 | 0 | 100.0000 | 7.79 |
| Run 8 | 11.38 | 1.17 | 14.50 | 0 | 100.0000 | 9.41 |

TABLE 4

Example 4
Tank Slurry, kg: 147
TSS, %: 3.5
Parent Gas: COMPRESSED AIR
Organics Added, ppmw: NONE

| Sample | Ozone Consumed (grams) | Ozone Conc. (% wt.) | Net Retention (min.) | Plate Count (CFU/ml) | Percent Bacteria Reduction | Passes Through Contactor |
|---|---|---|---|---|---|---|
| Run 1 | 0.00 | 1.00 | 0.00 | 110000 | 0.0000 | 0.00 |
| Run 2 | 0.83 | 1.08 | 1.00 | 110000 | 0.0000 | 0.50 |
| Run 3 | 2.56 | 1.12 | 3.00 | 900000 | −718.1818 | 1.50 |
| Run 4 | 3.70 | 1.17 | 5.00 | 3000 | 97.2727 | 2.49 |
| Run 5 | 4.81 | 1.27 | 7.00 | 100 | 99.9091 | 3.49 |
| Run 6 | 5.89 | 1.38 | 9.00 | 0 | 100.0000 | 4.49 |
| Run 7 | 8.02 | 1.37 | 13.00 | 0 | 100.0000 | 6.49 |

TABLE 5

Example 5

Tank Slurry, kg: 147
TSS, %: 3.5
Parent Gas: COMPRESSED AIR
Organics Added, ppmw: NONE

| Sample | Ozone Consumed (grams) | Ozone Conc. (% wt.) | Net Retention (min.) | Plate Count (CFU/ml) | Percent Bacteria Reduction | Passes Through Contactor |
|---|---|---|---|---|---|---|
| Run 1 | 0.00 | 1.57 | 0.00 | 11000 | 0.0000 | 0.00 |
| Run 2 | 0.40 | 0.93 | 1.00 | 13000 | −18.1818 | 0.50 |
| Run 3 | 0.79 | 0.92 | 2.00 | 3100 | 71.8182 | 1.00 |
| Run 4 | 1.29 | 0.98 | 3.00 | 0 | 100.0000 | 1.50 |
| Run 5 | 1.81 | 1.02 | 4.00 | 0 | 100.0000 | 2.00 |
| Run 6 | 2.29 | 0.97 | 5.00 | 500 | 95.4545 | 2.49 |
| Run 7 | 2.73 | 0.96 | 6.00 | 0 | 100.0000 | 2.99 |
| Run 8 | 3.18 | 1.03 | 7.00 | 130 | 98.8182 | 3.49 |
| Run 9 | 3.63 | 1.07 | 8.00 | 200 | 98.1818 | 3.99 |

TABLE 6

Example 6

Tank Slurry, kg: 147
TSS, %: 3.5
Parent Gas: COMPRESSED AIR
Organics Added, ppmw: NONE

| Sample | Ozone Consumed (grams) | Ozone Conc. (% wt.) | Net Retention (min.) | Plate Count (CFU/ml) | Percent Bacteria Reduction | Passes Through Contactor |
|---|---|---|---|---|---|---|
| Run 1 | 0.00 | 0.315 | 0.00 | 550000 | 0.0000 | 0.00 |
| Run 2 | 0.40 | 0.923 | 1.00 | 130000 | 76.3636 | 0.50 |
| Run 3 | 0.84 | 0.852 | 2.00 | 700 | 99.8727 | 1.00 |
| Run 4 | 1.63 | 0.777 | 4.00 | 300 | 99.9455 | 2.00 |
| Run 5 | 2.07 | 0.961 | 5.00 | 0 | 100.0000 | 2.49 |
| Run 6 | 2.47 | 0.845 | 6.00 | 100 | 99.9818 | 2.99 |
| Run 7 | 4.32 | 0.972 | 10.00 | 100 | 99.9818 | 4.99 |
| Run 8 | 5.09 | 0.872 | 12.00 | 0 | 100.0000 | 5.99 |

TABLE 7

Example 7

Tank Slurry, kg: 147
TSS, %: 3.5
Parent Gas: OXYGEN
Organics Added, ppmw: 1000

| Sample | Ozone Consumed (grams) | Ozone Conc. (% wt.) | Net Retention (min.) | Plate Count (CFU/ml) | Percent Bacteria Reduction | Passes Through Contactor |
|---|---|---|---|---|---|---|
| Run 1 | 0.00 | 4.78 | 0.00 | 750000 | 0.0000 | 0.00 |
| Run 2 | 1.27 | 3.97 | 1.00 | 25000 | 96.6667 | 0.50 |
| Run 3 | 2.96 | 4.02 | 2.00 | 95000 | 87.3333 | 1.00 |
| Run 4 | 4.57 | 4.04 | 3.00 | 3000 | 99.6000 | 1.50 |
| Run 5 | 7.02 | 3.82 | 4.00 | 350 | 99.9533 | 2.00 |
| Run 6 | 9.38 | 3.81 | 5.00 | 250 | 99.9667 | 2.49 |
| Run 7 | 11.40 | 3.99 | 6.00 | 0 | 100.0000 | 2.99 |

TABLE 8

Example 8

Tank Slurry, kg: 147
TSS, %: 3.5
Parent Gas: OXYGEN
Organics Added, ppmw: 1000

| Sample | Ozone Consumed (grams) | Ozone Conc. (% wt.) | Net Retention (min.) | Plate Count (CFU/ml) | Percent Bacteria Reduction | Passes Through Contactor |
|---|---|---|---|---|---|---|
| Run 1 | 0.00 | 5.19 | 0.00 | 170000 | 0.0000 | 0.00 |
| Run 2 | 4.33 | 3.87 | 2.00 | 75000 | 55.8824 | 1.00 |
| Run 3 | 9.27 | 3.87 | 4.00 | 750 | 99.5588 | 2.00 |
| Run 4 | 13.60 | 3.87 | 6.00 | 0 | 100.0000 | 2.99 |
| Run 5 | 14.49 | 4.02 | 7.00 | 330 | 99.8059 | 3.49 |
| Run 6 | 16.89 | 3.95 | 9.00 | 0 | 100.0000 | 4.49 |
| Run 7 | 19.26 | 3.88 | 11.00 | 0 | 100.0000 | 5.49 |
| Run 8 | 21.79 | 4.03 | 13.00 | 0 | 100.0000 | 6.49 |
| Run 9 | 24.94 | 3.82 | 15.00 | 0 | 100.0000 | 7.48 |

TABLE 9

Example 9
Tank Slurry, kg: 147
TSS, %: 3.5
Parent Gas: OXYGEN
Organics Added, ppmw: 1500

| Sample | Ozone Consumed (grams) | Ozone Conc. (% wt.) | Net Retention (min.) | Plate Count (CFU/ml) | Percent Bacteria Reduction | Passes Through Contactor |
|---|---|---|---|---|---|---|
| Run 1 | 0.00 | 3.33 | 0.00 | 150 | 0.0000 | 0.00 |
| Run 2 | 2.57 | 3.83 | 2.00 | 100 | 33.3333 | 1.00 |
| Run 3 | 5.85 | 3.92 | 4.00 | 0 | 100.0000 | 2.00 |
| Run 4 | 9.01 | 3.77 | 6.00 | 0 | 100.0000 | 2.99 |
| Run 5 | 12.20 | 3.84 | 8.00 | 3000 | −1900.00 | 3.99 |
| Run 6 | 14.69 | 3.82 | 10.00 | 0 | 100.0000 | 4.99 |
| Run 7 | 17.59 | 4.35 | 12.00 | 0 | 100.0000 | 5.99 |
| Run 8 | 20.39 | 3.70 | 14.00 | 0 | 100.0000 | 6.98 |
| Run 9 | 23.11 | 3.68 | 16.00 | 0 | 100.0000 | 7.98 |
| Run 10 | 26.56 | 3.87 | 18.00 | 0 | 100.0000 | 8.98 |
| Run 11 | 29.65 | 3.88 | 20.00 | 0 | 100.0000 | 9.98 |

TABLE 10

Example 10
Tank Slurry, kg: 170
TSS, %: 3.0
Parent Gas: OXYGEN
Organics Added, ppmw: 1500

| Sample | Ozone Consumed (grams) | Ozone Conc. (% wt.) | Net Retention (min.) | Plate Count (CFU/ml) | Percent Bacteria Reduction | Passes Through Contactor |
|---|---|---|---|---|---|---|
| Run 1 | 0.00 | 3.90 | 0.00 | 3100000 | 0.0000 | 0.00 |
| Run 2 | 2.12 | 4.60 | 1.00 | 14000000 | −351.6129 | 0.43 |
| Run 3 | 4.81 | 3.05 | 3.00 | 11000000 | −254.8387 | 1.29 |
| Run 4 | 7.95 | 3.11 | 5.00 | 5000000 | −61.2903 | 2.16 |
| Run 5 | 11.26 | 3.04 | 7.00 | 700000 | 77.4194 | 3.02 |
| Run 6 | 13.38 | 2.29 | 10.00 | 900000 | 70.9677 | 4.31 |
| Run 7 | 15.02 | 2.55 | 12.00 | 140000 | 95.4839 | 5.18 |
| Run 8 | 16.61 | 2.30 | 14.00 | 7000 | 99.7742 | 6.04 |
| Run 9 | 18.40 | 2.52 | 16.00 | 11000 | 99.6452 | 6.90 |

TABLE 11

Example 11
Tank Slurry, kg: 161
TSS, %: 3.0
Parent Gas: OXYGEN
Organics Added, ppmw: 1500

| Sample | Ozone Consumed (grams) | Ozone Conc. (% wt.) | Net Retention (min.) | Plate Count (CFU/ml) | Percent Bacteria Reduction | Passes Through Contactor |
|---|---|---|---|---|---|---|
| Run 1 | 0.00 | 3.27 | 0.00 | 1500000 | 0.0000 | 0.00 |
| Run 2 | 1.50 | 3.47 | 1.00 | 300000 | 80.0000 | 0.68 |
| Run 3 | 3.42 | 2.34 | 3.00 | 4500 | 99.7000 | 2.05 |
| Run 4 | 5.19 | 1.82 | 5.00 | 4000 | 99.7333 | 3.42 |
| Run 5 | 7.21 | 1.77 | 7.00 | 3900 | 99.7400 | 4.78 |
| Run 6 | 8.57 | 1.72 | 9.00 | 4000 | 99.7333 | 6.16 |
| Run 7 | 9.92 | 1.72 | 11.00 | 1000 | 99.9333 | 7.45 |
| Run 8 | 11.07 | 1.67 | 13.00 | 100000 | 93.3333 | 8.74 |

TABLE 12

Example 12
Tank Slurry, kg: 147
TSS, %: 5.0
Parent Gas: OXYGEN
Organics Added, ppmw: NONE

| Sample | Ozone Consumed (grams) | Ozone Conc. (% wt.) | Net Retention (min.) | Plate Count (CFU/ml) | Percent Bacteria Reduction | Passes Through Contactor |
|---|---|---|---|---|---|---|
| Run 1 | 0.00 | 3.63 | 0.00 | 50000 | 0.0000 | 0.00 |
| Run 2 | 1.24 | 3.47 | 1.00 | 2000 | 96.0000 | 0.55 |
| Run 3 | 3.62 | 2.67 | 3.00 | 300 | 99.4000 | 1.66 |
| Run 4 | 6.86 | 2.60 | 5.00 | 0 | 100.0000 | 2.76 |
| Run 5 | 10.14 | 2.61 | 7.00 | 0 | 100.0000 | 3.87 |
| Run 6 | 14.48 | 2.73 | 10.00 | 0 | 100.0000 | 5.52 |
| Run 7 | 17.31 | 2.70 | 12.50 | 0 | 100.0000 | 6.91 |
| Run 8 | 21.27 | 2.74 | 15.50 | 0 | 100.0000 | 8.56 |

TABLE 13

Example 13
Tank Slurry, kg: 125
TSS, %: 3.5
Parent Gas: OXYGEN
Organics Added, ppmw: NONE

| Sample | Ozone Consumed (grams) | Ozone Conc. (% wt.) | Net Retention (min.) | Plate Count (CFU/ml) | Percent Bacteria Reduction | Passes Through Contactor |
|---|---|---|---|---|---|---|
| Run 1 | 0.00 | 2.75 | 0.00 | 1000000 | 0.0000 | 0.00 |
| Run 2 | 1.22 | 2.74 | 1.00 | 500000 | 50.0000 | 1.10 |
| Run 3 | 4.29 | 2.48 | 3.00 | 50000 | 95.0000 | 3.30 |
| Run 4 | 6.49 | 2.56 | 5.00 | 100 | 99.9900 | 5.90 |
| Run 5 | 8.44 | 2.41 | 7.00 | 0 | 100.0000 | 8.25 |
| Run 6 | 10.51 | 2.52 | 9.00 | 0 | 100.0000 | 10.48 |

TABLE 14

Example 14
Tank Slurry, kg: 125
TSS, %: 3.5
Parent Gas: OXYGEN
Organics Added, ppmw: NONE

| Sample | Ozone Consumed (grams) | Ozone Conc. (% wt.) | Net Retention (min.) | Plate Count (CFU/ml) | Percent Bacteria Reduction | Passes Through Contactor |
|---|---|---|---|---|---|---|
| Run 1 | 0.00 | 1.505 | 0.00 | 700000 | 0.0000 | 0.00 |
| Run 2 | 0.96 | 1.211 | 2.00 | 700000 | 0.0000 | 1.32 |
| Run 3 | 2.33 | 1.142 | 5.00 | 15000 | 97.8571 | 3.30 |
| Run 4 | 3.64 | 1.173 | 8.00 | 10000 | 98.5714 | 5.28 |
| Run 5 | 4.74 | 1.271 | 11.00 | 9000 | 98.7143 | 7.26 |
| Run 6 | 6.91 | 1.268 | 15.00 | 6500 | 99.0714 | 9.90 |
| Run 7 | 8.39 | 1.412 | 18.00 | 7000 | 99.0000 | 11.88 |
| Run 8 | 9.71 | 1.406 | 21.00 | 7000 | 99.0000 | 13.86 |
| Run 9 | 10.94 | 1.382 | 24.00 | 4000 | 99.4286 | 15.84 |
| Run 10 | 12.80 | 1.296 | 28.00 | 1000 | 99.8571 | 18.48 |

The following Table 15 provides typical waste loading and flow rates for a commercial facility having the capacity of treating approximately 45,400 Kg of medical waste per 24 hour day under the assumptions that the slurry concentration in pulper 14 is 5% solids by weight and that the dewatering efficiency is 50%. Such loadings, flow rates and assumptions are merely representative and are not intended to limit the scope of the present invention or the appended claims.

TABLE 15

| | |
|---|---|
| 1. Waste feed to receiving hopper 1, Kg/min. | 32 |
| 2. Discharge of makeup pump 21, Kg/min. | 604 |
| 3. Fresh water makeup to makeup tank 15, Kg/min. | 29 |
| 4. Water velocity through eductor 22, m/sec. | 27 |
| 5. Differential pressure across eductor 22, Kg/cm² | 4.2 |
| 6. Air velocity into inlet of receiving hopper 1, m/sec. | 1 |
| 7. Slurry flow through transfer pumps 24 and 74, Kg/min. each | 1,460 |
| 8. Diameter of reactor vessels 28, 36, 43, 80, 87, m. | 1.8 |
| 9. Side water depth of reactor vessels 28, 36, 43, 80, 87, m. | 5.2 |
| 10. Capacity of reactor vessels 28, 36, 43, 80, 87, Kg. | 14,600 |
| 11. Volume of reactor vessels 28, 36, 43, 80, 87, l. | 13,300 |
| 12. Retention in each of reactor vessels 28, 36, 43, 80, 87, min. | 10 |
| 13. Slurry flow through pumps 33, 40, 57, 84, 95, Kg/min. | 1,460 |
| 14. Differential pressure across mixers 26, 34, 41, 78, 85, Kg/cm² | 4.2 |
| 15. Inlet diameter of mixers 26, 34, 41, 78, 85, cm. | 10 |
| 16. Orifice diameter of mixers 26, 34, 41, 78, 85, cm. | 2.5 |
| 17. Slurry velocity through mixers 26, 34, 41, 78, 85, m/sec. | 49 |
| 18. Diameter of reactor tubes 27, 35, 42, 79, 86, cm. | 15 |
| 19. Length of reactor tubes 27, 35, 42, 79, 86, m. | 5 |
| 20. Retention time in reactor tubes 27, 35, 42, 79, 86, sec. | 4.2 |
| 21. Ozone concentration (air as parent gas), % | 2 |
| 22. Ozone concentration (oxygen as parent gas), % | 5 |
| 23. Ozone production, gm/min. | 70 |
| 24. Gas flow (air as parent gas), Kg/min. | 3.5 |
| 25. Gas flow (oxygen as parent gas), Kg/min. | 1.4 |
| 26. Gas flow pressure, Kg/cm² | 0.7 |
| 27. Dewatered solids output, Kg/min. | 64 |
| 28. Water recycle, Kg/min. | 572 |

The invention being thus described, it will be apparent that the same may be varied in many ways. Such variations are not to be regarded as a departure from the spirit and scope of the invention and all such modifications are intended to be included within the scope of the claims.

What is claimed is:

1. A process for the continuous treatment of infectious waste material, which comprises:
   (a) introducing bulk unseparated infectious waste material comprising pulpable components and nonpulpable components into a receiving container means, said receiving container means being in communication with a primary shredding means whereby bulk unseparated infectious waste material supplied to said receiving container means is conducted to said primary shredding means;
   (b) shredding said bulk unseparated waste material by said primary shredding means;
   (c) transferring the shredded waste material from said primary shredding means to a pulping means having a means to provide a predetermined fluid level to said pulping means, said pulping means effective for repulping said pulpable components and creating a pulped slurry therefrom and also effective for creating a nonpulpable slurry from said nonpulpable components and separating said pulped slurry from said nonpulpable slurry;

(d) transferring said pulped slurry from said pulping means to a first reactor vessel means, said first reactor vessel means comprising a first reactor means communicating in series relationship with at least one second reactor means, and transferring said nonpulpable slurry from said pulping means to a separator means to separate and remove from said nonpulpable slurry glass and metal components contained therein and to form a separated nonpulpable slurry and thereafter transferring said separated nonpulpable slurry to a second reactor vessel means, said second reactor vessel means comprising a primary tank means communicating in series relationship with at least one second tank means;

(e) contacting, in said first reactor vessel means, said pulped slurry with a disinfecting fluid comprising ozone in gas phase and in aqueous solution, said contacting being achieved by flowing said pulped slurry and said disinfecting fluid through a mixer of said fist reactor means for mixing said pulped slurry with said disinfecting fluid and flowing the resulting mixture into said first reactor means of said first reactor vessel means, retaining the resulting mixture in said first reactor means for sufficient time to achieve at least partial disinfection of said pulped slurry and further discharging from said first reactor means undissolved gas which emits from the resulting mixture, said contacting being further achieved by additionally mixing said pulped slurry from said first reactor means with disinfecting fluid in a mixer of said at least one second reactor means and flowing the resulting mixture into said at least one second reactor means of said first reactor vessel means, retaining the resulting mixture in said at least one second reactor means for sufficient time to achieve substantially complete disinfection of said pulped slurry and further discharging from said at least one second reactor means undissolved gas which emits from the resulting mixture, and contacting, in said second reactor vessel means, said separated nonpulpable slurry from said separator means with said disinfecting fluid, said contacting being achieved by flowing said separated nonpulpable slurry and said disinfecting fluid through a mixer of said primary tank means for mixing said separated nonpulpable slurry with said disinfecting fluid and flowing the resulting mixture into said primary tank means of said second reactor vessel means, retaining the resulting mixture in said primary tank means for sufficient time to achieve at least partial disinfection of said separated nonpulpable slurry and further discharging from said primary tank means undissolved gas which emits from the resulting mixture, said contacting being further achieved by additionally mixing said separated nonpulpable slurry from said primary tank means with said disinfecting fluid in a mixer of said at least one second tank means of said second reactor vessel means and flowing the resulting mixture into said at least one second tank means, retaining the resulting mixture in said at least one second tank means for sufficient time to achieve substantially complete disinfection of said separated nonpulpable slurry and further discharging from said at least one second tank means undissolved gas which emits from the resulting mixture; and (f) transferring said disinfected pulped slurry from said at least one second reactor means and transferring said disinfected separated nonpulpable slurry from said at least one second tank means to dewatering means to remove liquid therefrom and to recover solid disinfected waste material.

2. The process of claim 1, wherein said infectious waste comprises an infectious medical waste.

3. The process of claim 1, wherein said primary shredding means is a rotary shear shredder, said primary shredding means being in communication with said receiving container means.

4. The process of claim 1, wherein said separated nonpulpable slurry is further shredded by a secondary shredding means to reduce the size of particles in said separated nonpulpable slurry prior to transferring said separated nonpulpable slurry into said second rector vessel means.

5. The process of claim 4, wherein said secondary shredding means is a rotary shear shredder, said secondary shredding means being in communication with said separator means.

6. The process of claim 5, wherein said separated nonpulpable slurry is further shredded by a tertiary shredding means to reduce the size of particles in said separated nonpulpable slurry, prior to transferring said separated nonpulpable slurry into said second reactor vessel means.

7. The process of claim 6, wherein said tertiary shredding means is a rotary shear shredder, said tertiary shredding means being in communication with said secondary shredding means.

8. The process of claim 1, wherein collectively said pulped and nonpulpable slurry comprises from about 1% to about 16% by weight shredded solids.

9. The process of claim 1, wherein said at least one second reactor means comprises from 1 to about 10 reactor vessels communicating in series relationship and said at least one second tank means comprises from 1 to about 10 reactor vessels communicating in series relationship.

10. The process of claim 1, wherein said disinfecting fluid of step (e) comprises ozone gas diluted in air.

11. The process of claim 1, wherein said ozone gas is present in a concentration of from about 0.5% to about 10% by weight of said disinfecting fluid.

12. The process of claim 1, wherein each of said pulped slurry and separated nonpulpable slurry is flowed through said first and second reactor vessel means, respectively, in a direction opposite to the buoyancy of ozone gas bubbles in contact with said pulped slurry and said separated nonpulpable slurry.

13. The process of claim 12, wherein each of said pulped slurry and said separated nonpulpable slurry is flowed downward through, respectively, said first and said second reactor vessel means at a nominal rate of about 1.1 meters per second.

14. The process of claim 1, wherein each of said pulped slurry and separated nonpulpable slurry is contacted with said disinfecting fluid for a period of from about 5 to about 45 minutes.

15. The process of claim 1, wherein the concentration of said ozone is continuously monitored by an analyzing means communicating with each of said first and second reactor vessel means, said analyzing means effective for monitoring and controlling the amount of disinfecting fluid introduced from a source thereof to said first and said second reactor vessel means and for monitoring the amount of disinfecting fluid utilized in said first and said second reactor vessel means.

16. The process of claim 1, further including the step of introducing said disinfecting fluid into said receiving container means to disinfect surfaces of said receiving container means.

17. An apparatus for the continuous treatment of infectious waste material, which comprises:
- (a) a receiving container means for receiving bulk unseparated infectious waste material comprising pulpable components and nonpulpable components;
- (b) a primary shredding means in communication with said receiving container means for reducing the particle size of said bulk unseparated infectious waste material and forming a shredded waste material;
- (c) a pulping means in communication with said primary shredding means, said pulping means having a fluid filling means for providing a predetermined fluid level in said pulping means, for repulping said pulpable components and creating a pulped slurry therefrom and also effective for creating a nonpulpable slurry from said nonpulpable components and separating said pulped slurry from said nonpulpable slurry;
- (d) a separator in communication with said pulping means for receiving said nonpulpable slurry from said pulping means and separating and removing therefrom glass and metal components contained therein thereby forming a separated nonpulpable slurry;
- (e) a reaction zone for disinfecting said pulped slurry and said separated nonpulpable slurry, said reaction zone comprising:
  - (i) a first reactor vessel means communicating with said pulping means for receiving said pulped slurry, said first reactor vessel means comprising a first reactor means communicating in series relationship with at least one second reactor means for disinfecting said pulped slurry;
  - (ii) a second reactor vessel means communicating with said separator for receiving said separated nonpulpable slurry, said second reactor vessel means comprising a primary tank means communicating in series relationship with at least one second tank means for disinfecting said separated nonpulpable slurry;
  - (iii) a disinfecting fluid generating means communicating with each of said first reactor vessel means and said second rector vessel means for continuously introducing a disinfecting fluid, comprising ozone in gas phase and in aqueous solution, into said first and second reactor vessel means, said first reactor means being provided with a mixer to mix said disinfecting fluid, comprising ozone in gas phase and in aqueous solution, into said first and second reactor vessel means, said first reactor means being provided with a mixer to mix said disinfecting fluid with said pulped slurry received from said pulping means, said at least one second reactor means being provided with a mixer to mix said disinfecting fluid with said pulped slurry received from said first reactor means, said primary tank means being provided with a mixer to mix said disinfecting fluid with said nonpulpable slurry received from said separator, said at least one second tank means being provided with a mixer to mix said disinfecting fluid with said nonpulpable slurry received from said primary tank means, each of said first reactor means and said at least one second reactor means being further provided with a discharge vent to discharge undissolved gas from said pulped slurry and each of said primary tank means and said at least one second tank means being further provided with a discharge vent to discharge undissolved gas from said nonpulpable slurry; and
- (f) dewatering means communicating with said first and second reactor vessel means, for receiving and recovering solid, disinfected waste material from the disinfected slurry.

18. The apparatus of claim 17, wherein said primary shredding means is a rotary shear shredder.

19. The apparatus of claim 17, further comprising a secondary shredding means in communication with said separator, for reducing the size of particles in said separated nonpulpable slurry prior to transferring said separated nonpulpable slurry into said second reactor vessel means.

20. The apparatus of claim 19, wherein said secondary shredding means is a rotary shear shredder.

21. The apparatus of claim 19, further comprising a tertiary shredding means in communication with said secondary shredding means, for further reducing the size of particles in said separated nonpulpable slurry prior to transferring said separated nonpulpable slurry into said second reactor vessel means.

22. The apparatus of claim 21, wherein said tertiary shredding means is a rotary shear shredder.

23. The apparatus of claim 17, wherein said at least one second reactor means comprises from 1 to about 9 second reactor means connected in series and said at least one second tank means comprises from 1 to about 9 second tank means connected in series.

24. The apparatus of claim 17, wherein each of said first reactor means, said at least one second reactor means, said primary tank means, and said at least one second tank means includes a reactor tube extending longitudinally from the top thereof, where said reactor tube is in connecting relation with a recirculation port, to a point proximate the bottom thereof.

25. The apparatus of claim 17, wherein said disinfecting fluid generating means comprises an ozone generator.

26. The apparatus of claim 17, further including a means communicating with said disinfecting fluid generating means and said receiving container means for flowing said disinfecting fluid to said receiving container means for disinfecting the surfaces thereof.

27. The apparatus of claim 17, further including an analyzing means communicating with said first and said second reactor vessel means and said generating means, for continuously monitoring and controlling the amount of disinfecting fluid introduced by said disinfecting fluid generating means and monitoring the amount of disinfecting fluid utilized in said first and second reactor vessel means.

* * * * *

UNITED STATES PATENT AND TRADEMARK OFFICE
CERTIFICATE OF CORRECTION

PATENT NO. : 5,173,257
DATED : December 22, 1992
INVENTOR(S) : Erich H. Pearson

It is certified that error appears in the above-indentified patent and that said Letters Patent is hereby corrected as shown below:

In column 5, line 49, after "hopper" delete "I" and insert therefor --1--

In column 9, line 9, after "gas bubbles," delete "ad" and insert therefor --and--

In column 14, line 28, delete "aeruoinosa" and insert therefor --aeruginosa--

In column 14, lines 62-63, after "chemical oxygen" delete "demane" and insert therefor --demand--

In claim 17, subpart (e)(iii), column 25, lines 60-64, delete "comprising ozone in gas phase and in aqueous solution, into said first and second reactor vessel means, said first reactor means being provided with a mixer to mix said disinfecting fluid"

Signed and Sealed this

Eighth Day of February, 1994

Attest:

BRUCE LEHMAN

Attesting Officer

Commissioner of Patents and Trademarks